United States Patent [19]

Kawasaki et al.

[11] Patent Number: 5,005,417
[45] Date of Patent: Apr. 9, 1991

[54] DETECTING FLAWS FORMED IN SURFACES OF ROTATING MEMBERS WITH ULTRASONIC WAVES

[75] Inventors: Keiji Kawasaki; Michio Sekiguchi, both of Nagoya; Tadaaki Matsuhisa, Kasugai, all of Japan

[73] Assignee: NGK Insulators, Ltd., Japan

[21] Appl. No.: 423,723

[22] Filed: Oct. 20, 1989

Related U.S. Application Data

[63] Continuation of Ser. No. 172,244, Mar. 23, 1988, abandoned.

[30] Foreign Application Priority Data

Mar. 31, 1987 [JP] Japan .................. 62-78277

[51] Int. Cl.$^5$ .................. G01N 29/04
[52] U.S. Cl. .................. 73/593
[58] Field of Search .................. 73/593, 598, 600, 622, 73/640, 641, 660

[56] References Cited

U.S. PATENT DOCUMENTS

| | | | |
|---|---|---|---|
| 2,912,853 | 11/1959 | Hanysz | 73/600 |
| 3,486,616 | 12/1969 | Brany et al. | 73/593 |
| 4,281,548 | 8/1981 | Köber | 73/593 |
| 4,286,467 | 9/1981 | Köber | 73/593 |
| 4,387,596 | 6/1983 | Fenkner et al. | 73/593 |

FOREIGN PATENT DOCUMENTS

| | | |
|---|---|---|
| 1294070 | 4/1969 | Fed. Rep. of Germany . |
| 3004079 | 8/1981 | Fed. Rep. of Germany . |
| 2953191 | 2/1982 | Fed. Rep. of Germany . |
| 0162952 | 8/1985 | Japan .................. 73/600 |
| 0209356 | 9/1986 | Japan .................. 73/600 |
| 2068550 | 8/1981 | United Kingdom . |

OTHER PUBLICATIONS

Moshfeghi, M. "NDT of Rods and Pipes Using Shear Wave Caustics" Ultrasonics, Jan. 1986, pp. 20–24.
"Ultrasound Tests Ball Bearings" RHP Ltd. Ultrasonics Nov. 1973 pp. 247–249.
diNovi, R. A. "Lamb Waves: Their Use in the Nondestructive Testing" Argonne National Laboratory, ANL6630, p. 13.
Krautkramer et al. "Ultrasonic Testing of Materials" 2nd Ed. pp. 426–435.
J. H. Krautkramer, "Werkstoffprufung mit Ultraschall", 1986, pp. 24–25 & 34–38.
"Ultrasonic Method for Inspecting Slab Mill Rollers", by V. E. Vinichenko Translated from Zavodskaya Laboratoriya vol. 32 No. 3 pp. 307–308, Mar. 1966.

Primary Examiner—Tom Noland
Assistant Examiner—Louis M. Arana
Attorney, Agent, or Firm—Arnold, White & Durkee

[57] ABSTRACT

In a method of detecting defects formed in a surface or in the vicinity thereof of a ball of a bearing by means of an ultrasonic wave, the ball and a probe for projecting an ultrasonic wave toward the ball and receiving an ultrasonic wave reflected from the detects are arranged in water in such a manner that a center axis of the probe is deviated from a normal axis of the ball which passes through a center of the ball and extends in parallel with the center axis of the probe by such a displacement amount that the ultrasonic wave refracted by the ball propagates along the surface of ball. The ball is rotated about a horizontal axis perpendicular to the normal axis, and the ball and probe are rotated relative to each other about a center axis of the ball which is perpendicular both to the normal axis and horizontal axis of the ball, so that the whole surface of the ball is scanned automatically with the ultrasonic wave.

20 Claims, 9 Drawing Sheets

FIG_1A
PRIOR ART
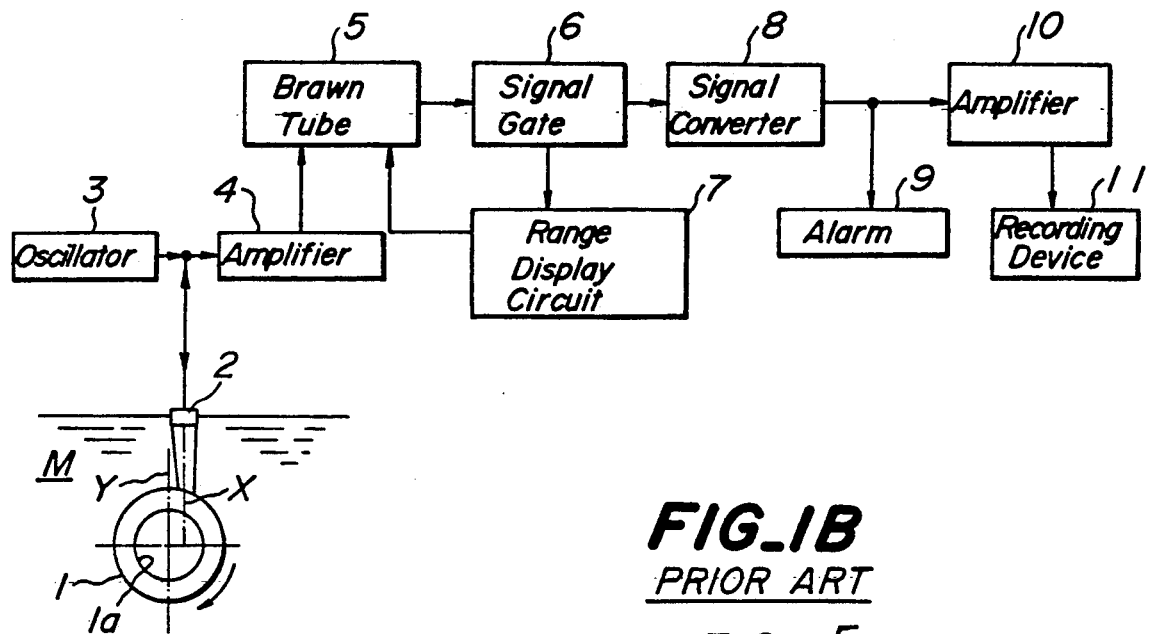
FIG_1B
PRIOR ART
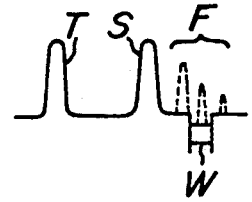
FIG_2
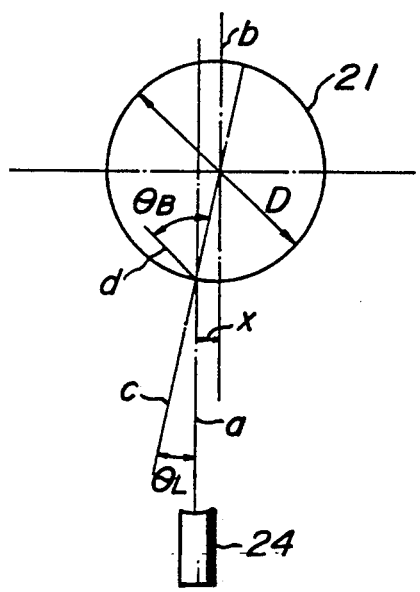

FIG_3
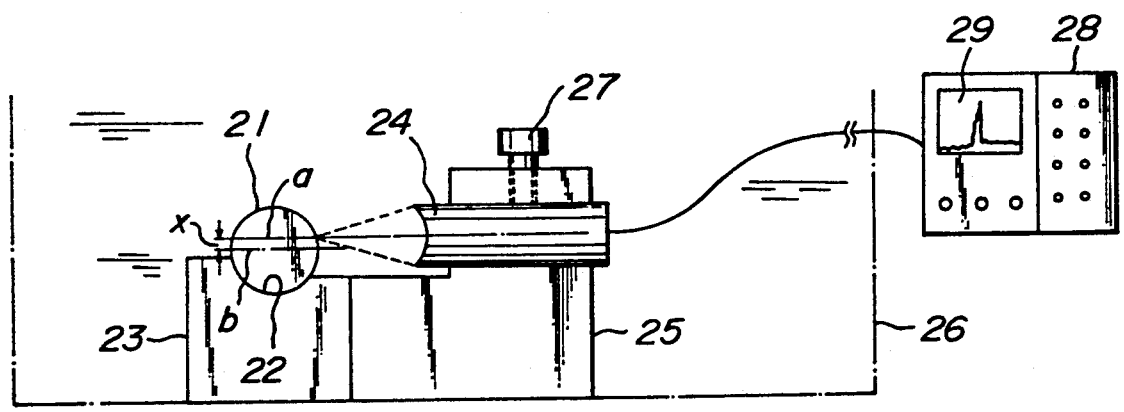

FIG_5
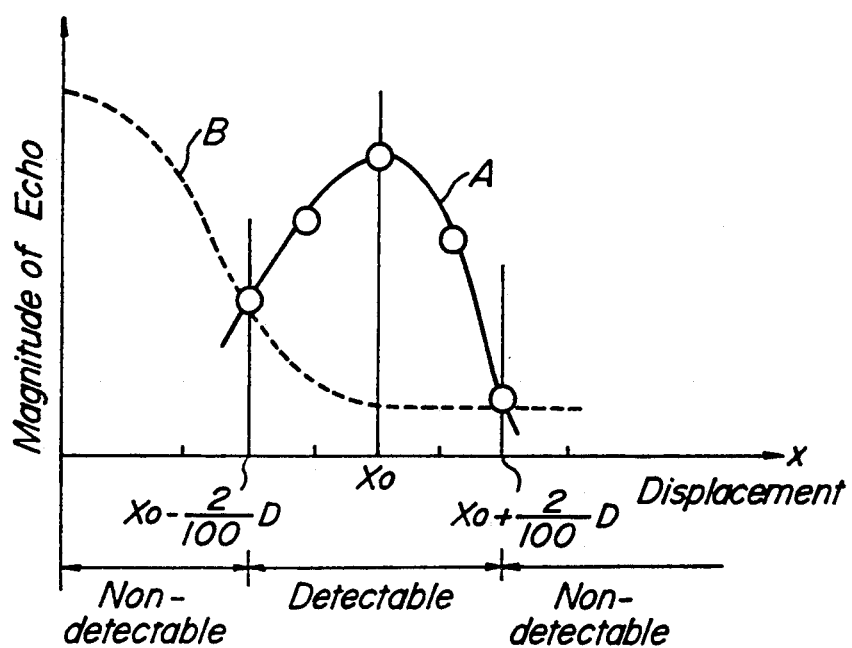
FIG_6
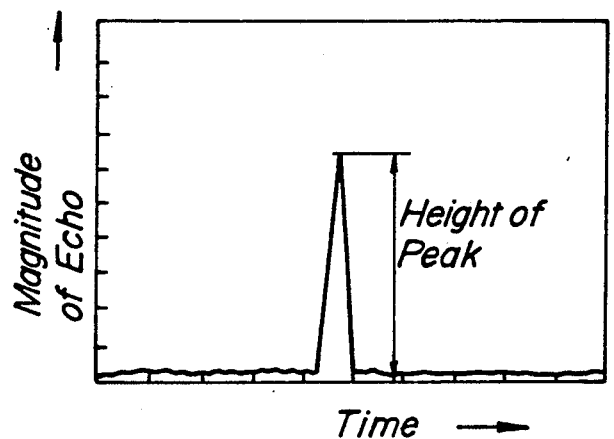

FIG_8

FIG_11

DETECTING FLAWS FORMED IN SURFACES OF ROTATING MEMBERS WITH ULTRASONIC WAVES

This is a continuation of application Ser. No. 07/172,244, filed Mar. 23, 1988, now abandoned.

BACKGROUND OF THE INVENTION

Field of the Invention and Related Art Statement

This invention relates to a method of detecting flaws or defects formed in a surface of a rotating member such as a ball or a cylindrical roller of a bearing with the aid of an ultrasonic wave, and an apparatus for carrying out such an ultrasonic flaw detecting method.

Flaws formed in a surface or bulk of a rotating bearing member have been tested or detected by an X-ray inspection technique, a fluorescent penetration inspection technique or by observing with a microscope or the naked eye.

However, these known techniques have some disadvantages in that a great deal of time is needed for testing, and it is impossible to detect fine flaws in the surface of the rotating bearing member. Especially, defects formed in the vicinity of the surface of the bearing member could not be effectively detected by means of conventional testing methods.

There has been also proposed an immersion type detection method which can detect flaws formed in the vicinity of an inner surface of a cylindrical member like a thin steel tube. Such a method has been described in a Japanese publication, "Ultrasonic Flaw Testing Method", edited by Steel Manufacture the 19th Committee of the Japan Society for the Promotion of Science, published by Nikkan Kogyo Shinbun-sha on July 30, 1974, pp. 491~493.

FIG. 1A is a schematic view showing the known immersion type ultrasonic flaw testing apparatus and FIG. 1B illustrates an echo signal appearing therein. In this method, a steel tube 1 to be tested is immersed in an ultrasonic wave propagating medium M such as water, and an ultrasonic wave is projected from a probe 2 toward the tube 1 by supplying an output signal of an oscillator 3 to the probe. The probe 2 is arranged off-axis with respect to the tube 1. That is to say, a center axis X of the ultrasonic wave is displaced from a vertical center axis Y of the steel tube 1 by such a distance that the ultrasonic wave penetrates into the tube and arrives at the inner surface 1a of the tube, and echoes reflected from the vicinity of the inner surface of the steel tube are received by the probe 2 as shown in FIG. 1B. Then an echo signal generated by the probe 2 is amplified by an amplifier 4 and then is displayed on a Brawn tube 5. At the same time, a range within which the flaws are to be detected is determined by a signal gate 6. The range thus determined is also displayed on the Brawn tube 5 through a detection range display circuit 7 as shown by a window W in FIG. 1B. In FIG. 1B, T denotes a transmitted pulse, S an echo signal reflected from the outer surface of tube and F represents an echo signal reflected from the bulk and inner surface of the tube. The echo signal selectively passed through the signal gate 6 is processed by a signal converter 8. When a flaw is detected within the selected range, an alarm is generated by an alarm 9, and the output signal from the signal converter is recorded by a recording device 11 via an amplifier 10.

By rotating the steel tube 1 in a direction shown by an arrow and moving the probe 1 in the longitudinal direction of the steel tube, any flaw formed in the vicinity of the inner surface 1a of the steel tube 1 can be tested continuously.

However, this known immersion type flaw detecting apparatus is designed to selectively detect flaws formed in the inner surface and the vicinity thereof of a steel tube, and the center axis X of the ultrasonic wave, i.e. the center axis of the probe 2 is laterally shifted from the vertical center axis Y of the steel tube 1 by such an amount that the ultrasonic wave can propagate efficiently within the tube up to the inner surface 1a of tube. Therefore, this known apparatus could not be utilized to detect flaws formed in an outer surface of tube or in the vicinity thereof. Particularly, this known apparatus is not suitable for detecting flaws formed in the surface of a rotating bearing member made of ceramics. In the rotating bearing member, defects formed in the vicinity of the outer surface thereof greatly affect the performance of the bearing.

SUMMARY OF THE INVENTION

The present invention has for its object to provide a novel and useful method for detecting defects formed in the vicinity of an outer surface of a rotating member such as balls and rollers of bearings, in which very fine defects can be accurately detected within a short time period.

According to the invention, a method of detecting a defect formed in a surface of a rotating member or in the vicinity thereof with the aid of a probe for emitting an ultrasonic wave toward the rotating member and receiving an ultrasonic wave reflected from the rotating member, comprises the steps of:

setting the probe with respect to the rotating member in an ultrasonic wave propagating medium such that a center axis (a) of the probe is deviated from a normal axis (b) which passes through a center axis of the rotating member and extends in parallel with said center axis of the probe by such a displacement amount (x) that the ultrasonic wave entered into the rotating member and refracted thereby propagates substantially along a surface of the rotating member;

projecting the ultrasonic wave from the probe toward the rotating member; and receiving an ultrasonic wave reflected from a defect formed in the surface of the rotating member or in a surface layer thereof having a thickness of about 2 mm.

The present invention also relates to an apparatus for detecting defects formed in an outer surface or in the vicinity thereof of a rotating member with the aid of an ultrasonic wave, and has an object to provide a novel apparatus in which any defects formed in the whole outer surface or in the vicinity thereof of a rotating member can be detected in a precise and speedy manner.

According to the invention an apparatus for detecting a defect formed in a surface of a rotating member or in the vicinity thereof with the aid of an ultrasonic wave comprises:

a probe for emitting an ultrasonic wave toward the rotating member and receiving an ultrasonic wave reflected from the defect;

first supporting means for supporting the rotating member rotatably about a center axis thereof;

second supporting means for supporting said probe with respect to the rotating member in such a manner that a center axis (a) of the probe is deviated from a normal axis (b) which passes through the center axis of the rotating member and extends in parallel with said center axis of the probe by such a predetermined displacement amount (x) that the ultrasonic wave entered into the rotating member and refracted thereby propagates substantially along a surface of the rotating member; and means for containing an ultrasonic wave propagating medium in which said probe, and said first and second supporting means are immersed.

In a preferred embodiment of the present invention, said displacement amount x (mm) satisfies the condition of $(D/2) \times (V_L/V_B) - D \times (2/100) \leq x \leq (D/2) \times (V_L/V_B) + D \times (2/100)$, wherein D (mm) presents a diameter of said rotating member, $V_B$ (m/sec) a velocity of shear ultrasonic wave traveling within a bulk material of the rotating member, and $V_L$ (m/sec) denotes a velocity of longitudinal ultrasonic wave traveling through the ultrasonic wave propagating medium.

In order to test the whole surface of the rotating member promptly without complex operation, there is provided means for rotating the rotating member. In a preferred embodiment of the invention, the rotating means comprises a supporting block, a hemispherical or semicylindrical concave surface formed in an upper surface of the supporting block, one or more slits formed in said concave surface and extending in a direction parallel to said normal axis of the rotating member, a conduit formed in the supporting block and communicated with said slits, and means for circulating the ultrasonic wave propagating medium through the slits and conduit so that the medium is ejected from the slits against the rotating member to rotate it.

In case of testing a cylindrical roller of a bearing, it is desired to provide a mechanism for moving the roller and the probe relative to each other in a longitudinal axis direction of the roller. Further, in case of testing a ball of a bearing, there is provided a mechanism for rotating the ball and the probe relative to each other about an axis which is perpendicular both to the center axis and the normal axis of the ball. In this manner, the whole surface of the roller or ball can be automatically tested in a prompt and accurate manner.

BRIEF DESCRIPTION OF THE DRAWINGS

FIG. 1A is a schematic view showing a principle of the known immersion type ultrasonic flaw detecting method;

FIG. 1B shows a waveform of an echo signal;

FIG. 2 is a schematic view for explaining a principle of the ultrasonic flaw testing method according to the invention;

FIG. 3 is a schematic view illustrating an embodiment of the ultrasonic flaw testing apparatus according to the present invention;

FIG. 5 is a graph illustrating the relationship between the displacement amount x and the magnitude of the echo reflected from the defect in the vicinity of the surface of the rotating member;

FIG. 6 shows a waveform of the echo signal displayed on the cathode-ray tube;

DETAILED DESCRIPTION OF THE PREFERRED EMBODIMENTS

Figure 4A:
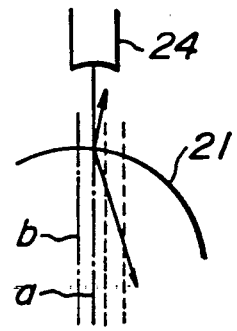
FIGS. 4A to 4F are schematic views and graphs showing the relationship between the displacement amount and the reflected ultrasonic echoes.

First, the principle of the ultrasonic flaw testing method according to the invention will be explained below with reference to FIG. 2.

In FIG. 2, it is assumed that a diameter of a rotating member 21 is D (mm), a displacement amount of a center axis a of a probe 24 from a normal axis b of the rotating member is x (mm), the velocity of a shear ultrasonic wave traveling through the bulk of the rotating member is $V_B$ (m/sec), the velocity of the longitudinal ultrasonic wave traveling through the ultrasonic propagating medium is $V_L$ (m/sec), an incident angle of the ultrasonic wave formed between the center axis a of the probe and a line c normal to the surface of rotating member is $\theta_L$, and a refracting angle of the ultrasonic wave formed between a center axis d of the refracted ultrasonic wave and said normal axis c is $\theta_B$. Then, there is obtained an equation $V_L/\sin \theta_L = V_B/\sin \theta_B$. This equation may be rewritten as follows; $\sin \theta_B = \sin \theta_L \times (V_B/V_L)$. In order to detect flaws formed in the surface of rotating member 21, the refracted ultrasonic wave has to propagate in a tangential direction, so that the refraction angle $\theta_B$ should be equal to 90°. If $\theta_B$ is set to 90° $\sin \theta_B$ becomes equal to 1, and therefore $\sin \theta_L \times (V_B/V_L)$ becomes also equal to 1. Thus, $\sin \theta_L = V_L/V_B = x/(D/2)$ is obtained, because $\theta_L \approx x(D/2)$. Therefore, when the displacement amount x is set to $(D/2) \times (V_L/V_B)$, the ultrasonic wave travels along the surface of rotating member 21. Consequently, fine defects formed in the surface of rotating member 21 can be detected.

Actually, the ultrasonic beam dispatched from the probe 24 has a definite thickness, so that fine defects not only in the surface of the rotating member but also in the vicinity thereof can be detected. If the diameter D of the rotating member is relatively large, it does not matter whether the diameter of ultrasonic beam is large or not. However, if the diameter of the rotating member is small, for example, 20 mm or less, it is desired to make the diameter of ultrasonic beam small, such that precise testing can be performed without being adversely influenced by noise. Therefore, it is desired to use a focusing-type probe in this case. For example, in the case that a bearing ball having a diameter of 10 mm is tested by the focusing-type probe having a focus diameter of 0.2~0.3 mm, fine defects having diameters of about 30 μm and formed in the surface or in a surface layer having a thickness of 1~2 mm can be precisely detected.

The experimental result about a range of the displacement amount between the center axis (a) of the probe and the normal axis (b) of the rotating member will be explained in detail in the following.

As shown in FIG. 3, a bearing ball 21 made of silicon nitride and having a diameter of 10 mm is rotatably held without play on a hemispherical recess 22 formed in a stop surface of a supporting member 23. A probe 24 is provided on a holding member 25. The supporting member 23 and holding member 25 are placed in a water tank 26 filled up with water. The probe 24 generates an ultrasonic wave having a frequency of 15 MHz, and has an ultrasonic transducer having a diameter of 6 mm and a focal length of 20 mm. The probe 24 is fixed to the holding member 25 by means of a screw 27 in such a manner that a distance between said probe 24 and the surface of bearing ball 21 can be adjusted. This distance has to be equal to the focal length of said probe 24. At first, the position of said holding member 25 with respect to the supporting member 23 is set such that the center axis a of the probe 24 is made coincident with the normal axis b of the bearing ball 21. The probe 24 is then connected to an ultrasonic tester 28 which is arranged outside the water tank 26. Electric power is then supplied to the tester 28, so that an ultrasonic wave is emitted from the probe 24 toward the ball 21, and a waveform of an echo reflected from the ball 21 is displayed and observed on a CRT monitor 29 provided in the tester 28. Thereafter, the displacement amount between the center axis a of said probe 24 and the normal axis b of said bearing ball 21 is adjusted by moving the holding member 25 gradually, while the waveform of echo is observed.

Figure 4B:
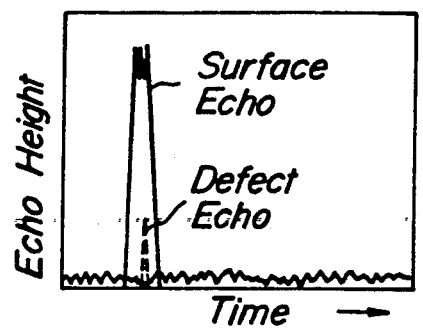
Figure 4C:
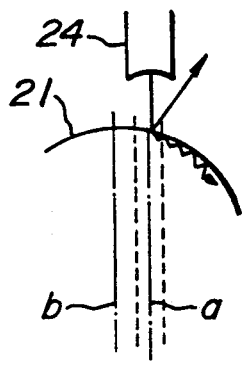
Figure 4D:
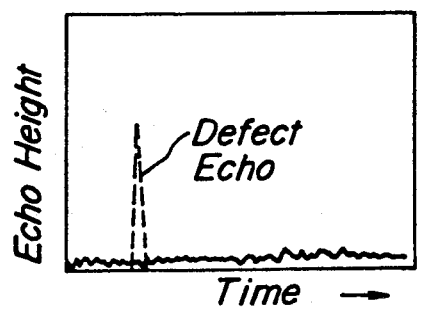

As a result, when the displacement amount x is smaller than $(D/2) \times (V_L/V_B) - D \times (2/100)$, an echo from a defect formed in the ball surface cannot be distinguished from a predominant echo from the surface of the ball because the ultrasonic wave is made incident upon the surface of the ball substantially perpendicularly thereto as illustrated in FIG. 4A. Therefore, the level of the echo signal of the ultrasonic wave reflected from the ball surface is much higher than that reflected from the defect as shown in FIG. 4B. On the other hand, when the displacement amount x satisfies a condition of $(D/2) \times (V_L/V_B) - D \times (2/100) \leq x \leq (D/2) \times (V_L/V_B) + D \times (2/100)$, the echo from the defect can be distinct from the echo from the surface of the ball, because the refraction angle of the ultrasonic wave is substantially equal to 90°, so that the ultrasonic wave travels along the ball surface as depicted in FIG. 4C. Further, the incident angle $\theta_L$ of the ultrasonic wave becomes larger such as about 13°~16°, so that the level of the echo reflected from the ball surface becomes low as shown in FIG. 4D.

Figure 4E:
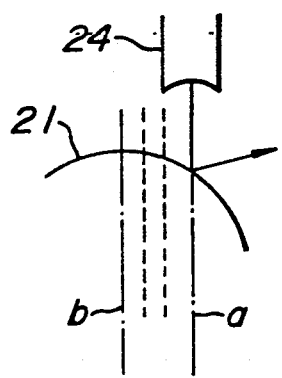
Figure 4F:
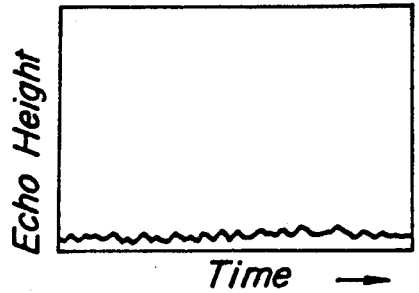

Furthermore, when the displacement amount x is made larger than $(D/2) \times (V_L/V_B) + D \times (2/100)$, the echo level from the defect cannot be distinct from the electric noise of the tester 28, because the refraction angle of the ultrasonic wave becomes larger than 90° so that the ultrasonic wave hardly penetrates into the bulk of ball and is reflected by the surface in a direction different from that toward the probe as shown in FIG. 4E, and therefore the echo level from the defect becomes very small as illustrated in FIG. 4F.

FIG. 5 is a graph showing the relationship between the displacement amount x and the magnitude of echo from the defect on the bearing ball 21 and interference noise. For the sake of simplicity, in this figure, $(D/2) \times (V_L/V_B)$ is represented by $X_o$. In FIG. 5, a solid curve A represents a magnitude of echo reflected from the defect in the surface of ball and a broken curve B denotes a magnitude of the noise. It is apparent from the graph that when the probe is so arranged that the displacement amount x between the center axis a of the probe and the normal axis b of the rotating member satisfies the following condition; $(D/2) \times (V_L/V_B) - D + (2/100) \leq x \leq (D/2) \times (V_L/V_B) + D + (2/100)$, it is possible to detect the defect formed in the surface or in the vicinity thereof of the bearing ball precisely without being affected by the noise.

Now the present invention will be further explained in detail with reference to the preferred embodiments illustrated in the drawings.

In a first embodiment, the ultrasonic flaw testing apparatus shown in FIG. 3 is used. The displacement amount x of the center axis a of the probe 24 with respect to the normal axis b of the ball 21 was set to 9.3 mm with a tolerance of ±0.2 mm.

This displacement amount x satisfies the condition of $(D/2) \times (V_L/V_B) - D \times (2/100) \leq x \leq (D/2) \times (V_L/V_B) + D \times (2/100)$, wherein the diameter of bearing ball is 10 mm; the velocity $V_L$ of the longitudinal ultrasonic wave traveling through the water is 1,500 m/sec.; and the velocity $V_B$ of shear ultrasonic wave traveling through the ball is 5,800 m/sec. The bearing ball was made of silicon nitride, and the ultrasonic frequency was set to 15 MHz. The probe 24 had the diameter of 6 mm and the focal length of 20 mm. The probe 24 was so positioned that the distance between the surface of bearing ball 21 and the probe 24 was made equal to the focal length of the probe 24. Next, the probe 24 was energized with the high frequency signal to generate the ultrasonic wave toward the ball 21. The echo reflected from the bearing ball 21 was detected by the probe and displayed on the CRT 29. While observing the ultrasonic echo waveform on the CRT, the ball was rotated by hand to scan the whole surface of the ball, and when a peak, as shown in FIG. 6, was displayed on CRT 29, a mark was recorded on the surface of bearing ball 21 at a relevant point.

Figure 7:
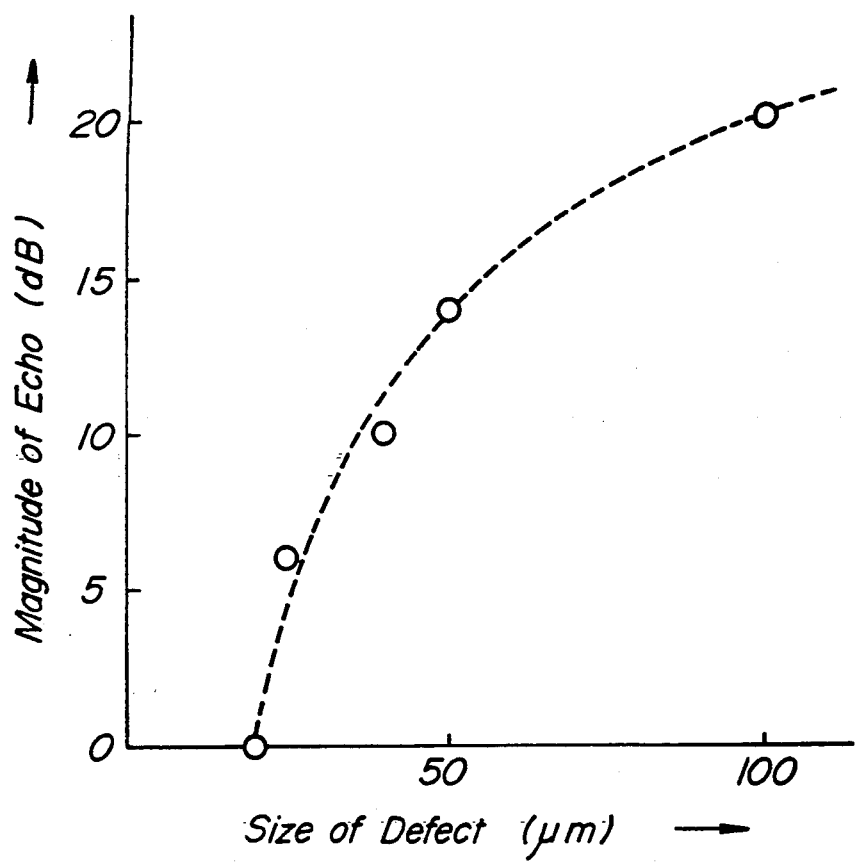
FIG. 7 is a graph illustrating the relationship between the size of the defect and the magnitude of echo from the defect.

After testing the whole surface of bearing ball 21 in this manner, the marked portions on the ball were observed with the aid of an optical microscope. As a result, defect like recesses were found and the dimensions thereof were measured. After testing ten balls in this manner, defects were found in five balls. FIG. 7 is a graph showing a relation between the magnitude of echo (dB) reflected from the defects of the five balls and sizes of defects ($\mu$m). It can be understood from FIG. 7 that fine defects having diameters of 30~100 $\mu$m can be detected in a precise manner.

Figure 8:
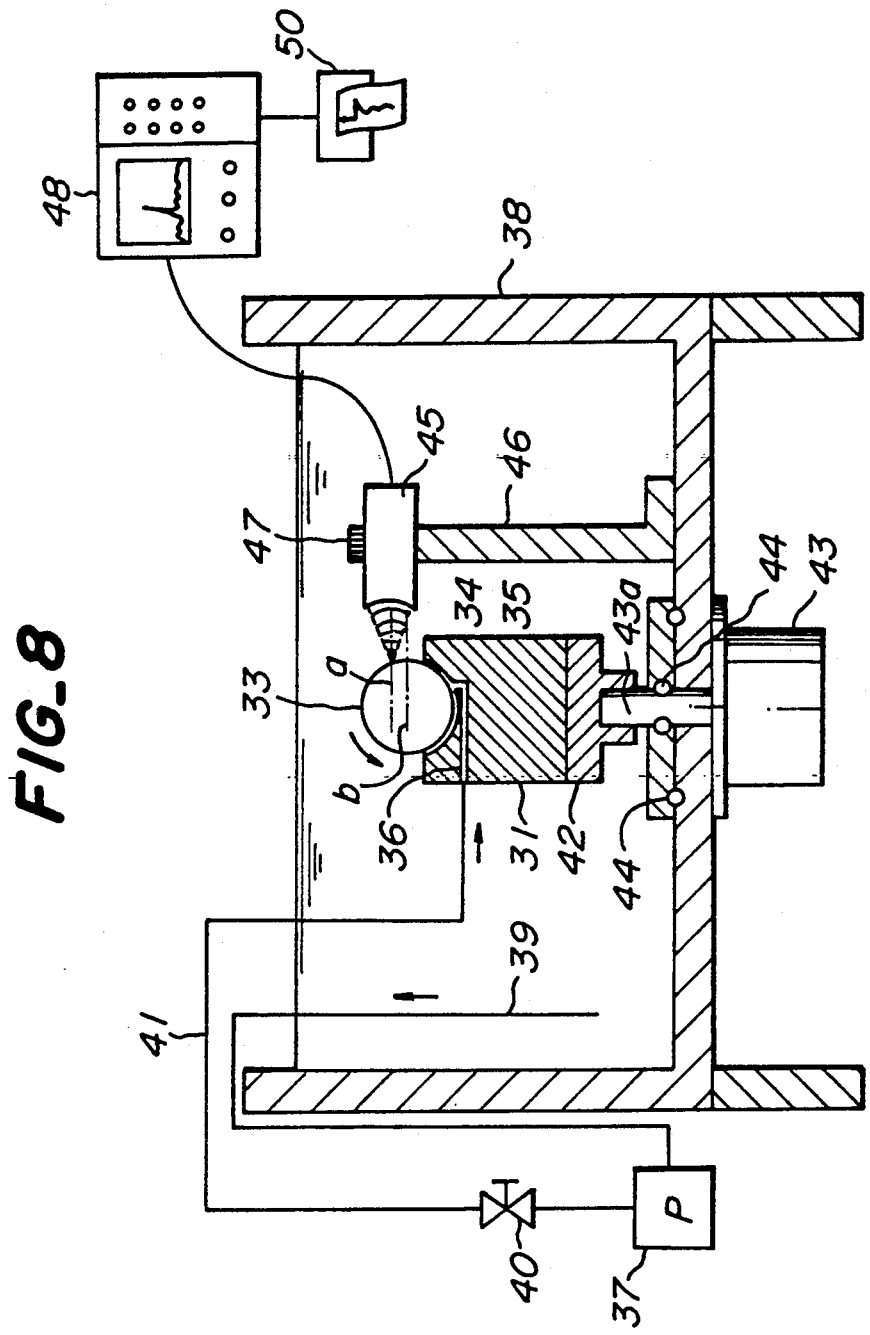
FIG. 8 is a cross sectional view illustrating another embodiment of the ultrasonic flaw detecting apparatus according to the present invention.
Figure 9:
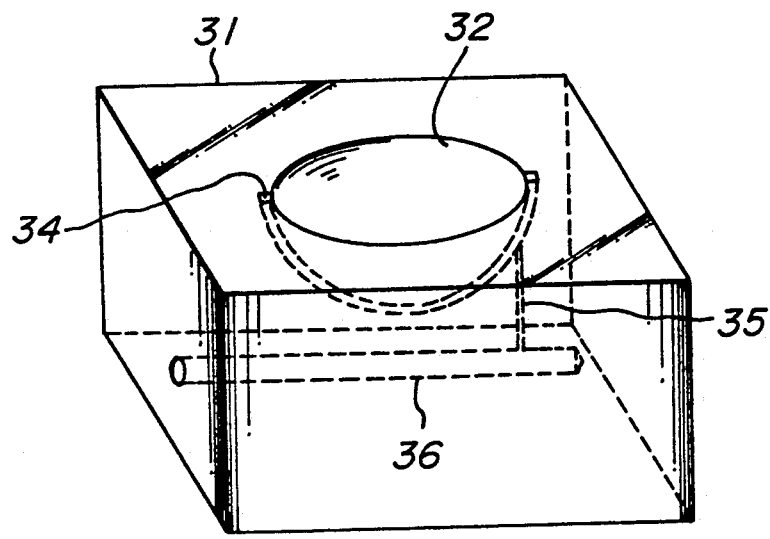
FIG. 9 is an enlarged perspective view showing the detailed construction of the ball supporting member shown in FIG. 8.

FIGS. 8 and 9 illustrate another embodiment of the ultrasonic flaw detecting apparatus. The apparatus comprises a ball supporting member 31 having a hemispherical recess 32 formed in an upper surface thereof. A ball 33 having a diameter of 10 mm is placed rotatably in the recess 32 without play. In the surface of the recess 32, there is formed a slit 34 having a width of 0.2 mm and depth of 0.5 mm. In the bulk of the supporting member 31, there are formed a thin conduit having a diameter of 0.2 mm and a thick conduit 36. One end of the thin conduit 35 is communicated to the slit 34 at a position thereof which is somewhat deviated rightward in FIG. 9, and the other end of the thin conduit is connected to the thick conduit 36.

FIG. 9 is an enlarged view showing the structure of said hemispherical recess 32, slit 34, and thin and thick conduits 35, 36 provided in the supporting member 31. The conduit 36 is connected to a pump (P) 37 arranged outside a water tank 38 through a tube 39 as shown in FIG. 8. The pump 37 is coupled via a valve 40 and tube 41 to the conduit 36. In order to rotate the ball 33 in the recess 32, the water in the tank 38 is circulated by the pump 37 through the conduits 36, 35 and slit 34. That is to say, the water is ejected from the slit 34 to rotate the ball 33 due to the viscosity of the water. The amount of water flowing through the fine conduit 35 is controlled by the valve 40 such that the ball is rotated at a velocity of 300 revolutions per minute.

In order to rotate reciprocally the ball 33, the supporting member 31 is secured to a turn table 42 and the turn table is coupled with a driving shaft 43a of an electric motor 43 which is arranged under the bottom of the water tank 38. Any spaces formed between the motor shaft 43a and the water tank 38 are sealed by O-rings 44 in order to prevent the leakage of the water.

Further, an ultrasonic flaw testing probe 45 comprising the ultrasonic transducer having a diameter of 6 mm, and a focal length of 20 mm is held by a probe stand 46. It should be noted that the position of probe 45 is so adjusted that the distance between the head of probe 45 and the surface of ball 33 faced thereto becomes equal to the focal length of the probe, and then the probe 45 is fixed to the stand 46 by means of a screw 47. Further, the probe 45 is connected to the ultrasonic tester 48 via a cable 49. The ultrasonic tester 48 is further connected to a pen-recorder 50.

In order to propagate the ultrasonic wave incident upon the ball 33 along the surface thereof, the center axis a of the probe 45 is deviated from the center axis b of the ball by an amount x equal to 1.3 mm±0.2 mm.

While the ultrasonic wave having frequency of 15 MHz is projected form the probe 45 toward the ball 33, the ball is rotated in the direction shown by an arrow at a velocity of 300 rpm, and at the same time the ball supporting block 31 is rotated by means of the motor 43 at a slow speed of 5 rpm over an angle of at least 180°.

In this manner, the whole surface of the ball 33 can be tested in an automatic manner. The echo signal generated by the probe 45 is displayed on a CRT monitor of the ultrasonic tester 48 and is also recorded on a record paper by the pen-recorder 50.

By using the above explained apparatus, ten balls made of silicon nitride were tested and echoes which were assumed to be reflected from defects were observed from three balls out of them. The surfaces of these balls were then observed with an optical microscope. A recess like defect was found in the surface of each of the three balls, while no defect was observed in the surfaces of the remaining seven balls.

Figure 10:
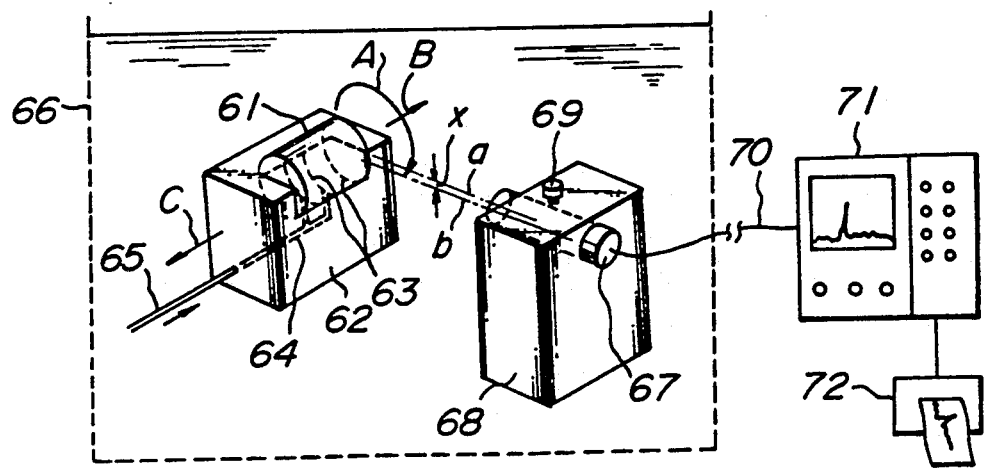
FIG. 10 is a schematic view illustrating another embodiment of the ultrasonic flaw testing apparatus according to the invention.

FIG. 10 is a schematic view illustrating another embodiment of the ultrasonic flaw testing apparatus according to the invention. In the present embodiment, a defect formed in a surface of a cylindrical roller of a bearing is to be detected. The roller 61 is supported rotatably without play on a substantially semicylindrical concave surface of a roller supporting member 62. In the semicylindrical surface of the supporting member 62, there are formed two slits 63 extending in the circumferential direction of the semicylindrical surface and these slits are communicated with a tube 65 by means of conduit 64 formed in the supporting member. Like as the embodiment illustrated in FIG. 8, the tube is coupled with a pump, so that the ultrasonic propagating medium such as water contained in a tank 66 is circulated via the slits 63 to rotate the roller 61 in a direction shown by an arrow A. An ultrasonic probe 67 is supported by a probe stand 68 and is fixed thereto by means of a screw 69. The probe 67 is connected to an ultrasonic tester 71 via a cable 70, and a pen-recorder 72 is connected to the ultrasonic tester 71.

In the present embodiment, the probe 67 is arranged with respect to the roller 61 such that the displacement amount x between the center axis a of the probe and the normal axis b of the roller is set to be 1.3 mm with a tolerance of ±0.2 mm, and a transducer of the probe is separated from the roller by a distance equal to a focal length of the transducer. The supporting member 62 is lineary and reciprocally moved as shown by arrows B and C by means of an electric motor not shown. The probe 67 of the present embodiment is the same as that of the previous embodiment. The roller 61 is rotated at a velocity of 300 rpm by ejecting the water from the slits 63, while the supporting member 62 is linearly moved at a velocity of 3 cm/sec.

Ten rollers made of silicon nitride were tested with the aid of the above explained apparatus. Then defect-like echoes were observed from four rollers out of them. Thus, when observing the cylindrical surface of these four rollers by an optical microscope, a recess-like defect was found in each surface of these four rollers. No defects were found in the cylindrical surfaces of the other six rollers.

Figure 11:
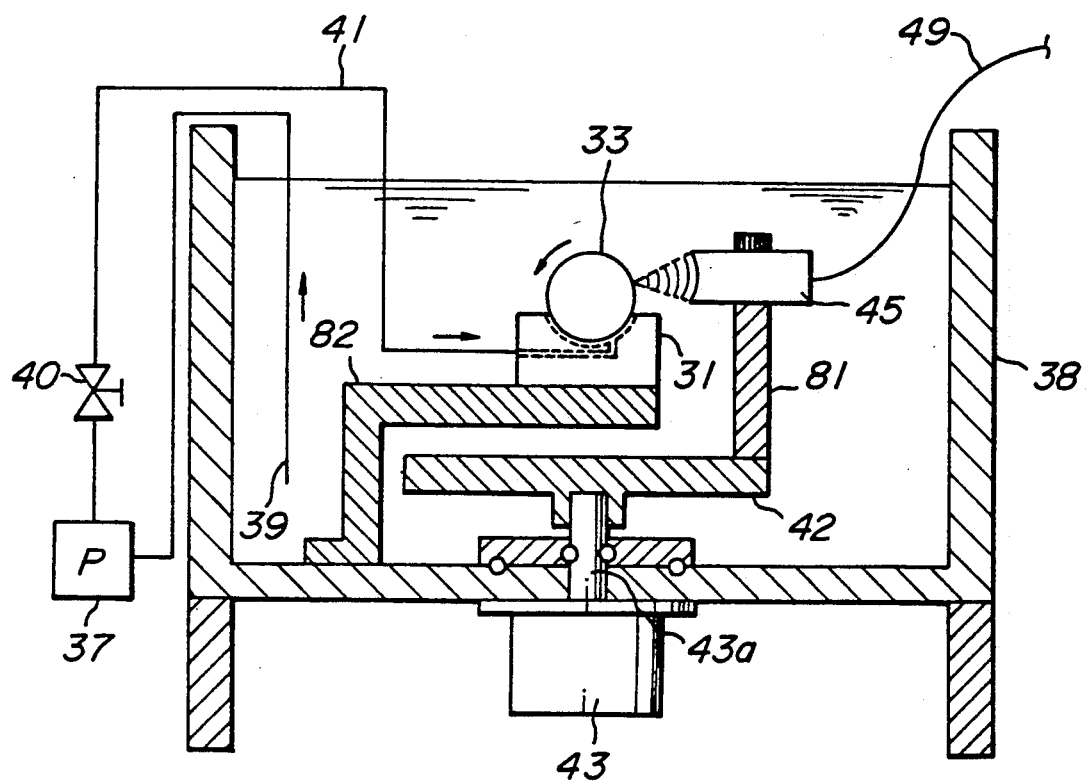
FIG. 11 is a cross sectional view illustrating another embodiment of the ultrasonic flaw detecting apparatus according to the present invention.

FIG. 11 is a cross sectional view showing another embodiment of the ultrasonic flaw testing apparatus according to the invention. Since this embodiment is similar to that illustrated in FIG. 8, portions similar to those shown in FIG. 8 are denoted by the same reference numerals used in FIG. 8 and thus a detailed explanation such portions is omitted. In the present embodiment, a probe 45 is supported by an arm 81 which is secured to a turntable 42. Therefore, the probe 45 is rotated by driving an electric motor 43 about a center of a ball 33 by substantially 180°. The ball 33 is rotated by circulating water contained in a tank 38 via tube 39, pump 37, valve 40, tube 41, and ball supporting member 31 in which conduits and slit are formed as shown in FIG. 9. The roll supporting member 31 is coupled with the tank 38 by means of stand 82. Also in this embodiment, the whole surface of the ball 33 can be automatically scanned and any defect formed therein or in the vicinity thereof can be detected in a prompt and precise manner.

Figure 12:
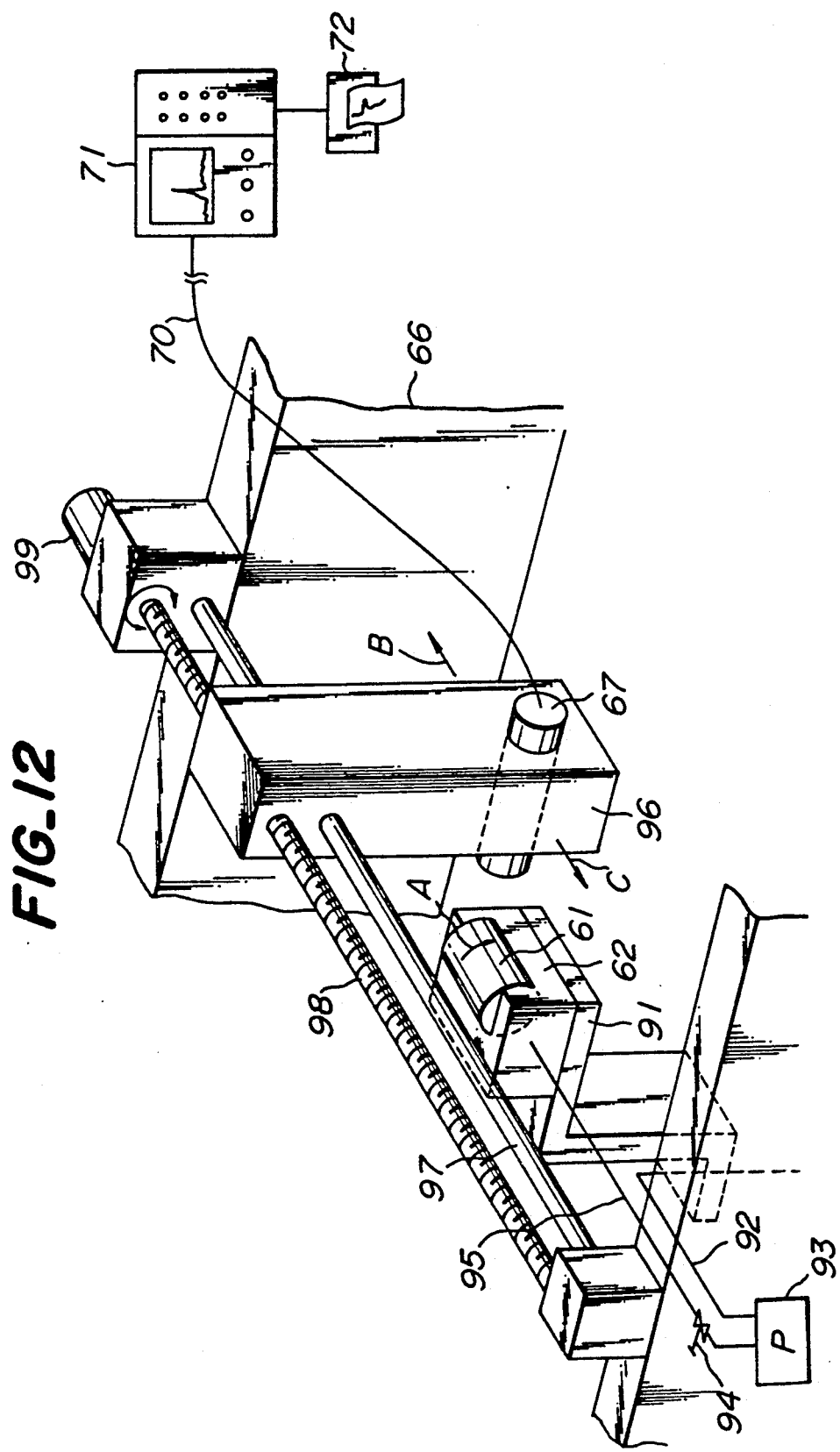
FIG. 12 is a perspective view depicting a major portion of still another embodiment of the ultrasonic flaw detecting apparatus according to the invention.

FIG. 12 shows a major part of still another embodiment of the ultrasonic flaw testing apparatus according to the invention. This embodiment is a modification of the embodiment shown in FIG. 10, and thus portions which are similar to those illustrated in FIG. 10 are represented by the same reference numerals as those used in FIG. 10. A cylindrical roller 61 of a bearing is rotatably supported by a roller supporting member 62 which is connected to a tank 66 by means of a stand 91. In the roller supporting member 62 there is formed a substantially semicylindrical concave surface on which the roller is placed, slits formed in the semicylindrical concave surface in a circumferential direction, and conduits in communication with the slits. The roller 61 is rotated in a direction shown by an arrow A by circulating a water contained in a tank 66 via tube 92, pump 93, valve 94, tube 95 and roller supporting member 62. In the present embodiment, instead of moving linearly the roller 61 in its axial direction, an ultrasonic probe 67 is moved linearly in parallel with the axial direction of the roller 61. To this end, the probe 67 is supported by a probe holder 96, and the holder is slidably secured to a guide shaft 97. There is further provided a lead screw 98 which is engaged with a nut secured to the probe holder 96. The lead screw 98 is rotated by an electric motor 99 so that the probe holder 96, i.e. the probe 67, is moved linearly in parallel with the axial direction of the cylindrical roller 61. In this manner, the whole surface of the cylindrical roller 61 can be automatically scanned with the ultrasonic beam, and any defect formed in the surface of the roller or in the vicinity thereof can be accurately detected.

Although the present invention may be used to detect defects formed in the surface of rotating members made of materials other than ceramics, it is preferable to apply the present invention to the rotating member made of ceramics, because even a fine defect in the surface thereof has a great influence upon the mechanical strength thereof. The rotating members made of ceramics, for example, silicon nitride, silicon carbide or zirconia are favorably used for bearings, abrasion resistance members, and sliding members, which require high mechanical strength and hardness.

Also, as an ultrasonic propagating medium, water is generally used. However, it is possible to use turbine oil or cylinder oil instead of water.

As explained above in detail, in the ultrasonic flaw testing method and apparatus according to the invention very fine defects having diameters of about 30 to 100 μm and formed in the surface of the ball or roller of bearings or in a surface layer having a thickness of about 2 mm can be accurately detected within a very short time period.

What is claimed is:

1. A method of detecting a defect formed in a surface of a rotating member having a circular cross-section with the aid of a focusing-type probe for emitting an ultrasonic wave toward the rotating member and receiving an ultrasonic wave reflected from the rotating member, comprising the steps of:

setting the focusing-type probe with respect to the rotating member in an ultrasonic wave propagating medium such that a center axis (a) of the probe is displaced from a normal axis (b) which passes through a center axis of the rotating member and extends parallel to said center axis of the probe by such a displacement about (x) that the ultrasonic wave is made incident upon the rotating member substantially at a critical angle of reflection, such that a portion of the ultrasonic wave is refracted thereby to propagate substantially along a surface of the rotating member as a surface wave, said probe being set at a distance from the surface of the rotating member which is substantially equal to the focal length of the ultrasonic wave emitted from the focusing-type probe, such that the ultrasonic wave to be projected from the probe is focused on the surface of the rotating member;

projecting the ultrasonic wave from the probe toward the rotating member; and receiving an ultrasonic wave reflected from a defect formed in the surface of the rotating member.

2. The method of claim 1, wherein said rotating member and probe are arranged such that the displacement amount x (mm) between the center axis of said probe and the normal axis of said rotating member satisfies the following condition:

$$(D/2) \times (V_L/V_B) - Dx(2/100) \leq x \leq (D/2) \times (V_L/V_B) + Dx(2/100)$$

wherein D (mm) represents a diameter of the rotating member, $V_B$ (M/sec) represents a velocity of a shear ultrasonic wave traveling within the rotating member, and $V_L$ (m/sec) represents a velocity of a longitudinal ultrasonic wave traveling through the ultrasonic wave propagating medium.

3. The method of claim 1, wherein said rotating member is a rotating ball bearing.

4. The method of claim 3 wherein said rotating bearing member comprises at least one ceramic selected from the group consisting of silicon nitride, silicon carbide and zirconia.

5. The method of claim 1, wherein the rotating member is rotated about a first rotation axis which is perpendicular to said normal axis (b).

6. The method of claim 5, wherein the rotating member is rotated by at least 180° about a second rotation axis which is perpendicular both to said normal axis (b) and said first rotation axis.

7. The method of claim 5, wherein said probe is rotated by at least 180° about a second rotation axis which is perpendicular both to said normal axis (b) and said first rotation axis.

8. The method of claim 1, wherein said rotating member is a rotating roller bearing.

9. The method of claim 8, wherein said roller bearing is rotated about a longitudinal axis thereof.

10. The method of claim 9, wherein said roller bearing is moved linearly in a direction along said longitudinal axis.

11. The method of claim 9, wherein said probe is moved linearly in a direction which is parallel to said longitudinal axis of the roller.

12. An apparatus for detecting a defect formed in a surface of a rotating member having a circular cross-section with the aid of an ultrasonic wave comprising:

a focusing-type probe for emitting a focused ultrasonic wave toward the rotating member and receiving an ultrasonic wave reflected from the defect;

first supporting means for supporting the rotating member rotatably about a center axis thereof;

second supporting means for supporting said focusing-type probe with respect to the rotating member in such a manner that a center axis (a) of the probe is displaced from a normal axis (b) which passes through the center axis of the rotating member and extends parallel to said center axis of the probe by such a predetermined displacement about (x) that the ultrasonic wave is made incident upon the rotating member substantially at a critical angle of reflection, such that a portion of the ultrasonic wave is refracted thereby to propagate substantially along a surface of the rotating member as a surface wave, said probe being set at a distance from the surface of the rotating member which is substantially equal to the focal length of the ultrasonic wave emitted from the focusing-type probe, such that the ultrasonic wave projected from the probe is focused on the surface of the rotating member; and means for containing an ultrasonic wave propagating medium in which said probe, said first supporting means and said second supporting means are immersed.

13. The apparatus of claim 12, wherein said displacement amount (x) mm of the center axis (a) of said probe and the normal axis (b) of said rotating member satisfies the following condition:

$$(D/2) \times (V_L/V_B) - Dx(2/1000) \leq x \leq (D/2) \times (V_L/V_B) + Dx(2/100),$$

wherein D (mm) represents a diameter of the rotating member, $V_B$ (m/sec) represents a diameter of the rotating member, $V_B$ (m/sec) represents a velocity of a shear ultrasonic wave traveling within the rotating member, and $V_L$ (m/sec) represents a velocity of a longitudinal ultrasonic wave traveling through the ultrasonic wave propagating medium.

14. The apparatus of claim 13, wherein said second means for supporting the probe comprises a stand for supporting the probe slidably in a direction of said center axis of the probe and means for fixing the probe to the stand, so that a distance between the rotating member and the probe is set to equal a focal length of the ultrasonic wave emitted from the focusing-type probe.

15. The apparatus of claim 13, for detecting defects on the rotating member in the form of a ball, further comprising:
    first rotating means for rotating the ball about the center axis thereof; and
    second rotating means for rotating the ball about an axis which is perpendicular both to the normal axis and the center axis of the ball by a least 180°.

16. The apparatus of claim 15, wherein said first rotating means comprises a supporting block, a substantially hemispherical concave surface formed in an upper surface of the supporting block for supporting the ball rotatably without play, a slit formed in the hemispherical concave surface and extending in a direction parallel to said normal axis, a conduit formed in said supporting block in communication with said slit, and means for circulating the ultrasonic wave propagating medium through said conduit and slit to form a jet flow for rotating the ball.

17. The apparatus of claim 13, for detecting defects on the rotating member in the form of a ball, further comprising:
    first rotating means for rotating the ball about the center axis thereof; and
    second rotating means for rotating the probe about an axis which is perpendicular both to the normal axis and the center axis of the ball by a least 180°.

18. The apparatus of claim 13, for detecting on the rotating member in the form of a cylindrical roller, further comprising:
    rotating means for rotating the roller about a longitudinal axis thereof; and
    means for linearly moving the roller in a direction parallel to the longitudinal axis of the roller by a distance at least equal to a whole length of the roller.

19. The apparatus of claim 18, wherein said rotating means comprises a supporting block, a substantially semicylindrical concave surface formed in an upper surface of the supporting block, said roller being placed on the semicylindrical concave surface without play, at least one slit formed in said semicylindrical concave surface and extending in a direction parallel to the normal axis (b), a conduit formed in the supporting block in communication with said slit, and means for circulating the ultrasonic wave propagating medium through said conduit and slit to form a jet flow for rotating the roller.

20. The apparatus of claim 13, for detecting defects on the rotating member in the form of a cylindrical roller, further comprising:
    rotating means for rotating the roller about a longitudinal axis thereof; and
    means for linearly moving the probe in a direction parallel to the longitudinal axis of the roller by a distance at least equal to a whole length of the roller.

* * * * *

UNITED STATES PATENT AND TRADEMARK OFFICE
CERTIFICATE OF CORRECTION

PATENT NO. : 5,005,417

DATED : April 9, 1991

INVENTOR(S) : Keiji KAWASAKI et al.

It is certified that error appears in the above-identified patent and that said Letters Patent is hereby corrected as shown below:

ON THE TITLE PAGE:
In section [30] Foreign Application Priority Data, change "62-78277" to --62-78227--.

Signed and Sealed this

Twenty-ninth Day of September, 1992

Attest:

DOUGLAS B. COMER

Attesting Officer

Acting Commissioner of Patents and Trademarks